United States Patent [19]

Picot et al.

[11] Patent Number: 5,505,204
[45] Date of Patent: Apr. 9, 1996

[54] ULTRASONIC BLOOD VOLUME FLOW RATE METER

[75] Inventors: Paul A. Picot; Aaron Fenster, both of London, Canada

[73] Assignee: University Hospital (London) Development Corporation, Ontario, Canada

[21] Appl. No.: 242,107

[22] Filed: May 13, 1994

[30] Foreign Application Priority Data

May 13, 1993 [GB] United Kingdom .................. 9309861

[51] Int. Cl.⁶ ...................................................... A61B 8/00
[52] U.S. Cl. ...................................................... 128/661.1
[58] Field of Search ..................... 128/661.08, 661.09, 128/661.1, 916; 73/861.25

[56] References Cited

U.S. PATENT DOCUMENTS 4,913,159  4/1990  Gardin et al. ...................... 128/661.1
5,409,010  4/1995  Beach et al. ...................... 128/661.09

OTHER PUBLICATIONS

Japanese Circulation Journal, vol. 54, Mar. 1990, "Quantitative Color Flow Imaging to Measure the Two-dimensional Distribution of Blood Flow Velocity and the Flow Rate", Kitabatake et al., pp. 304–308.

Ultrasound in Med. & Biol., vol. 18, No. 5, 1992, "A Velocity Evaluation Phantom for Colour and Pulsed Doppler Instruments", Rickey et al., pp. 479–494.

Primary Examiner—George Manuel
Attorney, Agent, or Firm—Staas & Halsey

[57] ABSTRACT

A volume flow meter for displaying two-dimensional volume flow through a vessel, comprising an ultrasound instrument with scan head, a location and orientation sensor mounted to the scan head, and a computer connected to the ultrasound instrument and the sensor. The scan head is adapted to be positioned adjacent the vessel under investigation, for generating a raster of pixels which defines a color image representing flow velocities in the vessel through an image plane of the scan head. The sensor measures position and orientation of the scan head in three dimensions and generates a signal representative thereof to the computer. The computer receives said raster of pixels and the signal from the sensor and in response calculates the position and orientation of the vessel axis in three-dimensions responsive to orientation of the image plane longitudinally of the vessel. The computer then determines an angle θ between this axis and the image plane responsive to orientation of the image plane transversally to the vessel. Finally, the computer calculates and displays the volume flow as a summation of the flow velocities scaled by the tangent of the angle θ.

4 Claims, 3 Drawing Sheets a) pre-op baseline: 61 mLmin⁻¹ b) post-catheter: 46 mLmin⁻¹ c) post-angioplasty: 158 mLmin⁻¹ d) after 15 min.: 56 mL min⁻¹

ULTRASONIC BLOOD VOLUME FLOW RATE METER

FIELD OF THE INVENTION

This invention relates in general to medical diagnostic equipment, and more particularly to an ultrasonic blood volume flow rate meter using transverse colour Doppler ultrasound.

BACKGROUND OF THE INVENTION

Non-invasive Doppler sonography is widely accepted as a means of measuring blood velocity. However, in some situations, the volume flow rate of blood may be a better indicator of the state of disease. One potential application of volume flow measurements is the prediction of stenosis of both common and internal carotid arteries by monitoring common carotid blood flow. In principle, an adequate degree of stenosis (generally accepted as 50% diameter reduction), results in a measurably decreased volume flow. Investigators have attempted to quantify this volume flow reduction using different sonographic techniques, with varying degrees of success. Some authorities have suggested that the ratio of flows of the unaffected and stenotic carotid arteries is the best predictor of carotid stenosis. Volume flow measurements have also been suggested as a technique for short- and long-term follow-up of carotid endarterectomy.

Volume flow measurements may also be applied in the diagnosis and treatment of vascular malformations. Specifically, the measurement of volume flow may help to distinguish arteriovenous malformations and fistulae, which are high-flow lesions, from venous malformations, which are low-flow lesions. Moreover, volume flow measurements provide a quantitative way both of assessing blood steals and of evaluating the effectiveness of embolization therapy. Renal dialysis patients may also benefit from Doppler volume flow measurements. Either inadequate or excessive flow through angioaccess fistulae can have pernicious clinical consequences. Doppler sonography has been suggested as a way of quantifying this flow.

Several techniques have been developed to estimate blood volume flow from Doppler velocity measurements, each being characterized by certain advantages and disadvantages. Generally, in order to estimate the volume flow rate of blood through an artery, pulsed Doppler ultrasound is used to measure the velocity of the blood. From this velocity measurement, and a measurement of the diameter of the vessel, an estimate of the volume of blood flowing through the vessel may be made. This volume flow estimation technique assumes a parabolic blood velocity profile, and assumes a circular vessel. Other techniques, such as colour M-mode, directly measure the one-dimensional velocity profile, but still assume a circular artery. Still other techniques exist, (e.g. those using uniform insonation of a vessel), but are also prone to measurement uncertainties.

Thus, it is known in the art to approximate blood velocity measurements across an entire blood vessel lumen by using only a single-point velocity measurement from a conventional clinical ultrasound instrument at the centre of the vessel and assuming a parabolic velocity profile.

Previous attempts to measure blood flow from two-dimensional velocity profiles have proven to be inaccurate because of the difficulty in determining Doppler angle (see Akira Kitabatake "Quantitative Color Flow Imaging to Measure the Two-Dimensional Distribution of Blood Flow Velocity and the Flow Rate", Japanese Circulation Journal, Vol. 54 March 1990.)

SUMMARY OF THE INVENTION

According to the present invention, a clinical colour Doppler ultrasound instrument is utilized with a position and orientation sensing device, and a computer with video digitizer to acquire blood velocity measurements in two dimensions across an entire blood vessel lumen. The blood velocity profile measured using the system of the present invention permits the precise determination of the volume flow rate of blood through the vessel.

The use of a position and orientation measurement device permits the accurate determination of Doppler angle required to make an accurate volume flow measurement, thereby removing the vessel circularity assumption of Kitabatake et al, and its attendant errors. The volume flow rate is determined according to the present invention by integrating the two-dimensional velocity profile over the vessel lumen area. The volume flow rate measurements are then displayed to an operator in real time as a scrolling graph, and in terms of cycle-to-cycle volume flow in mL/min.

A benefit of this transverse-image based approach is that, unlike prior art single-point or colour M-mode techniques, the volume flow estimate is not as sensitive to the positioning of the ultrasound transducer. This useful property arises because the flow is properly recorded using the system of the present invention for blood vessels appearing anywhere within the active 'colour' area of the ultrasound image. This removes one aspect of operator-induced variability in the blood flow estimate, and permits long-duration flow studies to be performed without the need to continually monitor transducer positioning.

BRIEF DESCRIPTION OF THE DRAWINGS

Details of the present invention are provided herein below with reference to the following drawings, in which.

DETAILED DESCRIPTION OF THE PREFERRED EMBODIMENT

Figure 1:
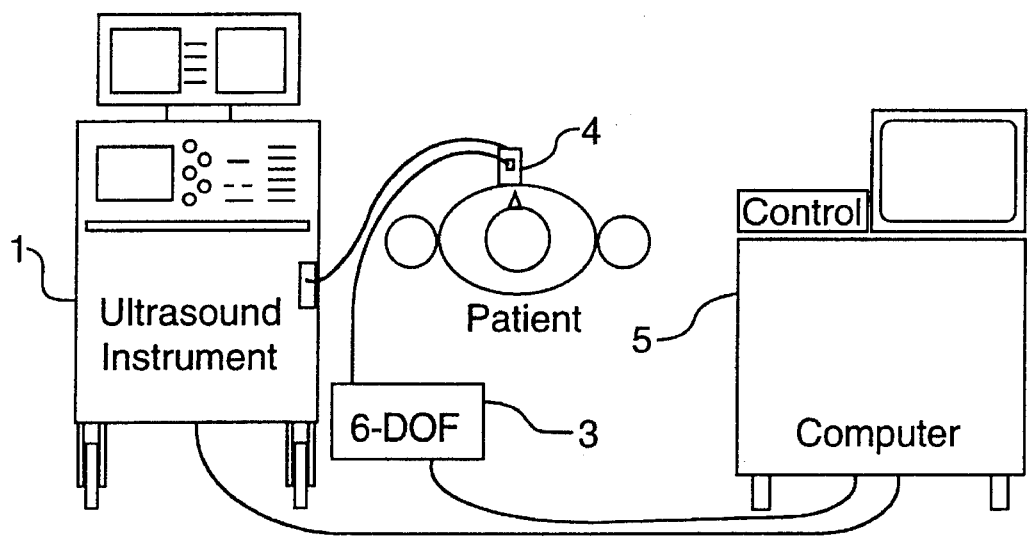
FIG. 1 is a schematic representation of an ultrasonic blood volume flow rate meter according to the present invention.

FIG. 1 shows the components of the invention, and their arrangement. A clinical diagnostic ultrasound imaging instrument 1 generates ultrasound images which are then used for measuring blood velocity virtually simultaneously over large areas in these images. Commercially available colour Doppler ultrasound instruments may be used for this purpose (eg. ATL Ultramark 9). In such well known systems, ultrasound images are generated in which human anatomy (eg. vessel wall, fat, etc.) is represented by black and white images (with various intermediate shades of grey), while different velocities of blood flow are represented by different colours.

A position and orientation sensing device 3 is connected to the ultrasound instrument 1. The sensing device 3 comprises a transmitter positioned at a fixed location near the patient, and a receiver mounted on the ultrasound instrument scan head 4. One suitable position and orientation sensing device is the Flock of Birds six-degree-of-freedom measuring device manufactured by Ascension Technology Corporation of Burlington, VT. In this device, the transmitter generates a pulsed DC magnetic field, and the receiver (comprising three orthogonal coils), detects the magnetic field generated by the transmitter and senses both the location of the receiver in three-dimensions, as well as its orientation relative to the transmitter. The location is measured in terms of X, Y and Z positional coordinates of the receiver with respect to the transmitter, while the orientation angles are defined in terms of rotations about the Z, Y and X axes of the receiver. These angles are referred to as azimuth, elevation and roll in Euler angle nomenclature.

A computer 5 (eg. 80386-based PC), with added commercially available digitizer (eg. Vision 16 Frame Grabber manufactured by Vision Technologies of Fremont, Calif.), custom-written software, monitor, and operator controls, is connected to the ultrasound instrument 1 and sensing device 3. The location and orientation data generated by the sensing device 3 may be transmitted digitally from the receiver to the computer 5 via either a full duplex RS232C interface or a half duplex RS422/485 interface, in a well known manner.

Figure 2:
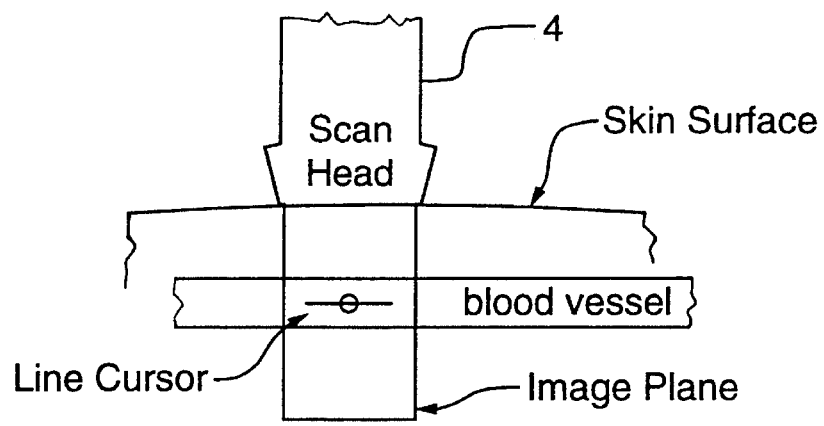
FIG. 2 shows the position of an ultrasound scan head and position of a line cursor according to the method of using the system of the present invention.

In operation, the ultrasound instrument operator locates a blood vessel of interest in a patient while viewing the colour Doppler ultrasound image on the computer monitor, and positions the scan head 4 so as to produce a longitudinal image of the vessel on the monitor, that is, an image with the blood vessel axis within the plane of the image, as shown in FIG. 2. This image is termed the "landmark". The operator then manually positions a line cursor on a blood vessel in the image. The sensing device 3 affixed to the ultrasound instrument scan head 4, continually reports to the computer 5 the position and orientation of the scan head. Using the location and orientation of the scan head measured by the sensor 3, and the location and orientation of the vessel axis image in the two-dimensional image plane as given by cursor location chosen by the operator, the computer 5 calculates the location of the axis of the blood vessel in three-dimensional space.

Figure 3:
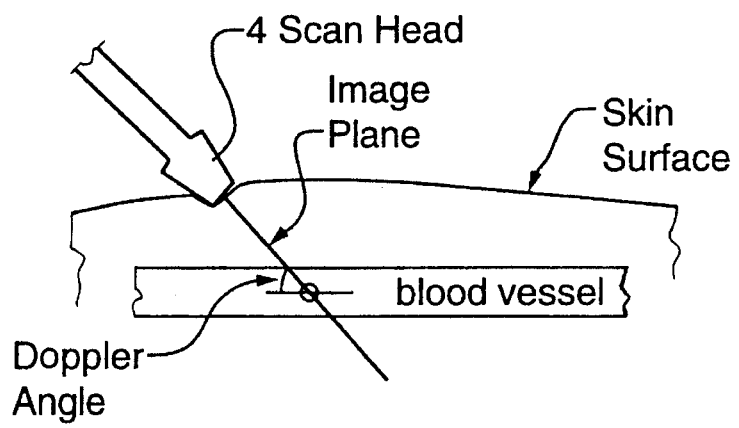
FIG. 3 shows the scan head of FIG. 2 oriented at an angle to the axis of the blood vessel according to the method of using the system of the present invention.

Next, the operator rotates the scan head 4 on the patient's skin surface to produce a transverse image of the blood vessel, that is, an image with the blood vessel axis passing through the image plane at an angle referred to herein as the "Doppler angle", as shown in FIG. 3. This position of the scan head 4 allows the determination of velocity across the complete two-dimensional cross-section of the blood vessel, and the simultaneous measurement of the functional cross-sectional area of the vessel (i.e. the area in which the measured velocities are non-zero).

The sensor 3 continues to communicate to the computer 5 the location and orientation of the scan head 4. The computer 5 continually calculates the angle between the image plane and the blood vessel axis (i.e. the "Doppler angle") using transverse image geometry. The computer 5 uses the measured Doppler angle, velocity measurements in the blood vessel being made by the ultrasound instrument 1, and the functional cross-sectional area of the vessel, to calculate the volume of blood passing through the ultrasound image plane. This calculation is performed approximately 10 to 30 times per second, depending on the speed of the ultrasound instrument 1.

The volume flow, Q, through the artery (assuming axial flow) is given by the flow though the plane, and is equal to the sum of the entire velocity profile cutting through the plane:

$$Q = \tan e \sum_{i=0}^{npix} V_i \Delta A$$

where e designates the Doppler angle, and is given by the angle between the ultrasound image plane and the vessel axis; $V_i$ is the measured Doppler velocity at each pixel obtained from the digitized colour (ie. the internal digitizer in computer 5 digitizes the Red-Green-Blue (RGB) colour video output from ultrasound instrument 1 and converts the colour image to a two-dimensional velocity map); $\Delta A$ is the pixel area in the image plane; and, npix is the number of pixels with colour.

The resulting two-dimensional velocity profile per image is scaled by the pixel size, tangent of the Doppler angle, and image period (ie. frame rate) to yield a volume flow graph and numerical value which are presented to the operator via the computer monitor (or via a scrolling print-out) in real time, as discussed in greater detail below with reference to FIGS. 4 and 5.

The measured Doppler velocity $V_i$ at each pixel can be calculated using known velocity calibration techniques such as disclosed in Rickey, D. W. and Fenster, A., "A Velocity Evaluation Phantom for Colour and Pulsed Doppler Instruments", Ultrasound Med. Biol., 18:479–494, 1992. Another technique is to assume that individual colours represent respective velocities based on the technical specifications of the clinical ultrasound instrument 1. The computer 5 is then able to calculate individual velocities by accessing an internal look-up table which associates the colours appearing in the ultrasound image with the calibrated velocities. This calculation is performed on a pixel-by-pixel basis from the colour image raster received from the ultrasound instrument 1.

This volume flow determination is performed at the same rate as the image acquisition on the ultrasound instrument 1, (i.e. 10 to 30 measurements per second). The volume flow information is presented to the operator on the monitor or in hard copy in a well known fashion, namely in a flow-rate versus time graph, as well as a numerical result, in millilitres per minute, or millilitres per cardiac cycle.

The flow rate may be measured at 10 to 30 times per second for as long as desired, making possible long duration monitoring of flow, for example, during surgery or stress testing.

The apparent size of the blood vessel being imaged changes depending on the amount of acoustic power received from it, due to the sensitivity profile of the ultrasound transducer array of scan head 4. Higher returned acoustic power causes an apparent spreading and increase in size of the vessel being imaged, and thus an artefactual increase in the measured volume flow rate. Also, intreventing tissue or fat can decrease the received power, and therefore decrease the measured flow. For consistent volume flow measurements, then, it is important to adjust the output power or colour gain of the ultrasound instrument 1 to fix the average returned power from the vessel of interest at a predetermined value. For the purposes of these measurements, the colour gain and output power controls can be considered equivalent over most of the power range that is encountered. To measure the returned power from a blood vessel, the operator temporarily places the instrument 1 in power-measurement mode. The colour power image produced by the instrument 1 in this mode is measured by the computer 5 by a colour-to-power mapping technique similar to the velocity measurement technique described above. The computer 5 measures the returned power and displays the value in bar-graph form. The operator then manually adjusts the acoustic power or colour gain to place the bar-graph into a suitable target zone. The power level of the target zone can be determined using in-vitro tests. The operator then places the ultrasound instrument 1 in velocity-measurement mode to continue with the flow measurement.

Figure 4:
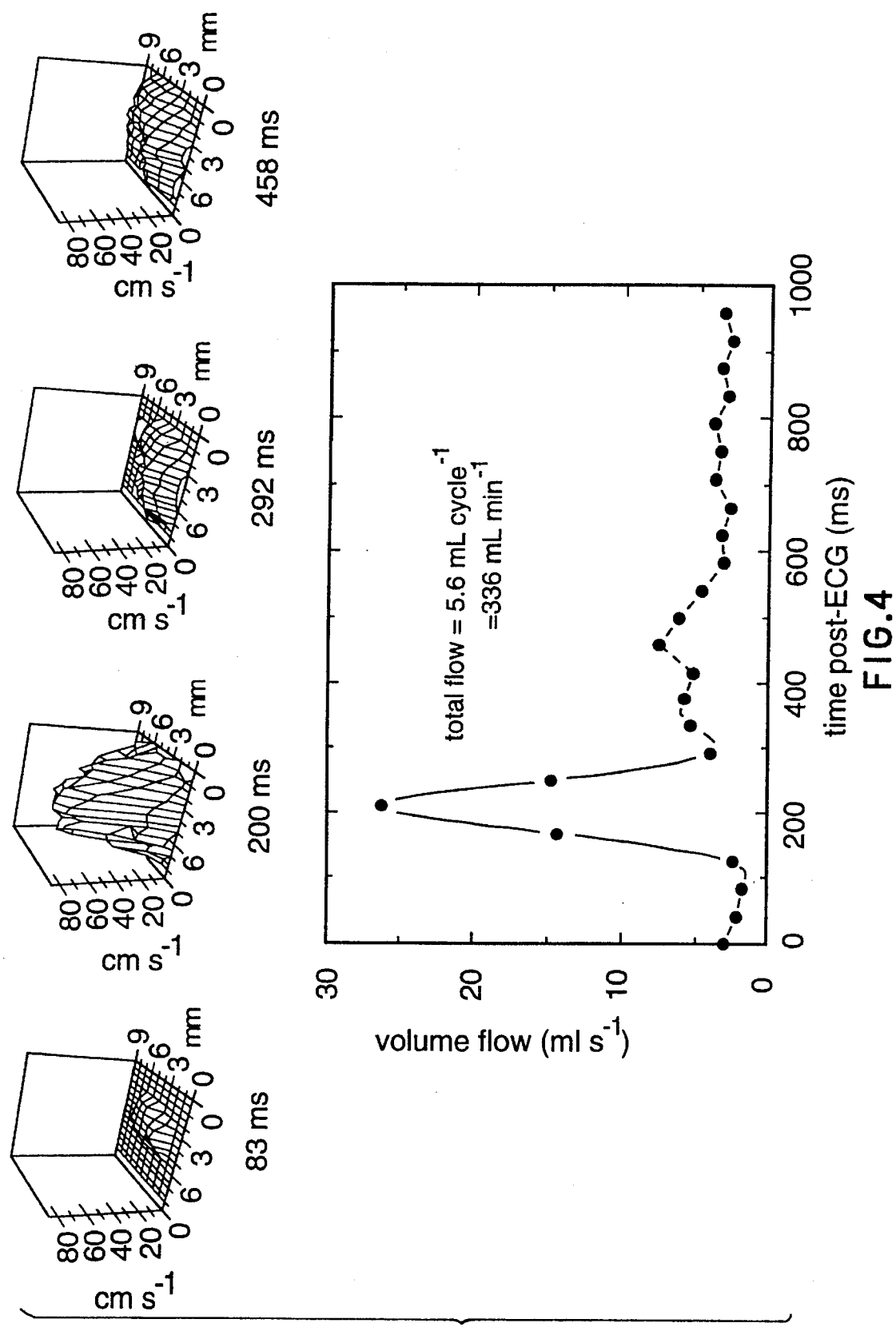
FIG. 4 is a graph showing volume blood flow rate measured in a human carotid artery over a single cardiac cycle.

FIG. 4 shows an example of the volume flow rate measurement in a human carotid artery. Selected measured two-dimensional velocity profiles are shown at the top of FIG. 4, and the series of volume flows computed from a series of these velocity profiles form the ensemble shown in the graph. In the example shown, there were twenty four measurements made over a single cardiac cycle lasting one second. The units appearing on the time axis are in milliseconds post 'R'-wave of the ECG. The integral flow through this cycle was 5.6 mL. The heart rate at the time was 60 beats per minute. The volume flow rate was thus 336 mL/min. The graph shows both the variation in flow rate over the cycle, as well as the net volume flow during that cycle. According to the present invention, the length of a sequence is limited only by storage memory capacity of the host computer 5. Thus, several-hour runs are possible for long-duration studies. The maximum sample rate is governed by the video frame rate (eg. 30 frames per second in the configuration of the preferred embodiment).

Figure 5A:
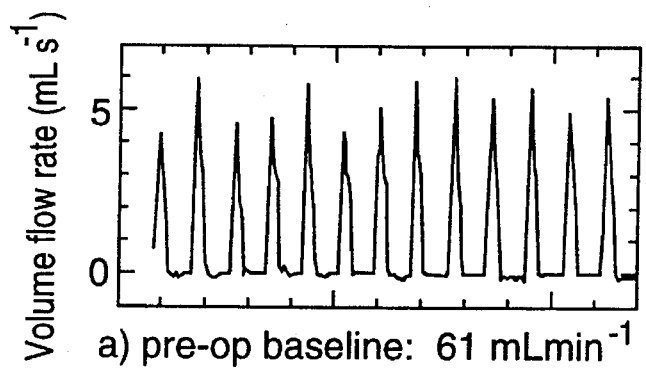
FIGS. 5a, 5b, 5c and 5d represent a blood volume flow record obtained at various times during a femoral artery angioplasty procedure.
Figure 5B:
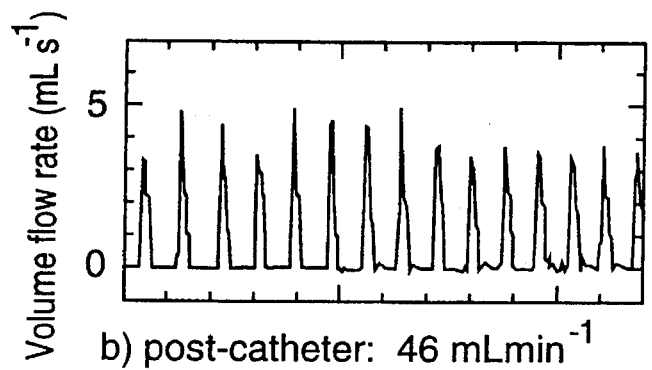
Figure 5C:
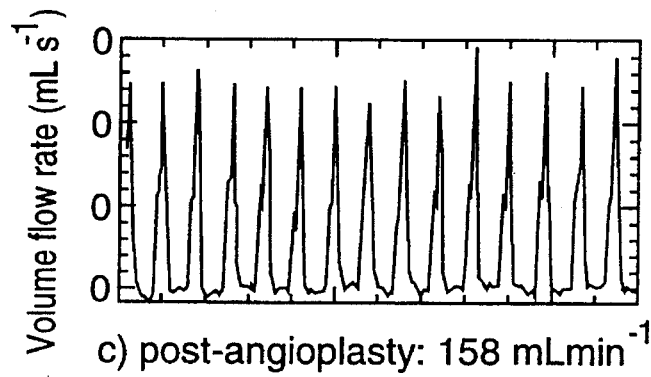
Figure 5D:
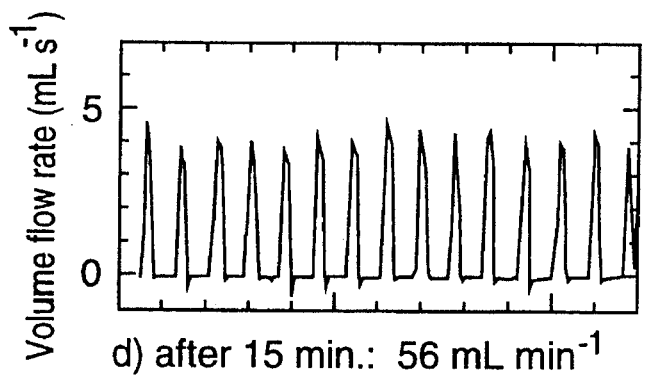

FIGS. 5a through 5d show in-vivo volume flow measurement of a patient during femoral angioplasty procedures, using the device of the present invention. Each volume flow measurement consisted of two 15-second flow recordings (for the determination of the true Doppler angle and true volume flow), which resulted in a total of two additional minutes to the normal procedure time. FIGS. 5a and 5b show the results of measurements obtained immediately proximal to a stenosis prior to the angioplasty. FIG. 5c shows an increase in resting flow two minutes post-angioplasty, with injection of nitroglycerin. After a resting period, flow returned to pre-operative levels as shown in FIG. 5d.

In summary, the volume flow measurement technique of the present invention removes assumptions about vessel circularity and is not sensitive to simple changes in position of the scan head 4, unlike prior art single-point Doppler flow measurement systems. Since the two-dimensional velocity profile is directly measured, the system of the present invention also removes assumptions of velocity profile shape (typically assumed in the prior art to be parabolic). However, this volume-flow measurement approach makes several implicit assumptions. It assumes that all the flow streamlines in a vessel at the measurement site are parallel, so that they all have the same Doppler angle. This implies that a relatively straight vessel is required, that the flow is neither converging or diverging significantly, and that there be little turbulence. Post-stenotic measurements, and measurements in highly diseased parts of vessels may be inaccurate due to unknown and time-varying Doppler angles. It is also assumed that the ultrasound sample volumes (voxels) are small compared to the vessel, so that the vessel is sampled at several locations across its diameter. To measure accurately pulsatile flows, the ultrasound instrument 1 must maintain a frame rate which is sufficient to record rapidly-changing blood velocities. We have measured the power spectrum of pulsatile flow in healthy volunteers, and found that a sample rate of 24 frames per second is sufficient to adequately sample the velocities. From the constraints described herein, we have concluded that the system of the present invention is best suited to blood flow measurements in substantially straight vessels, such as the carotid artery.

Alternatives, modifications and further applications of the invention are possible. For example, although the preferred embodiment of the invention has been described in relation to sensing blood volume flow in humans. The principles of this invention may be applied to blood volume flow in animals, and may even be applied to the sensing of liquid flow in industrial processes (ie. non-medical application). These and other embodiments and applications of the invention are possible within the sphere and scope of the invention as defined by the claims appended hereto.

We claim:

1. A volume flow meter for measuring and measuring and displaying volume flow through a vessel having an axis, comprising:

a) an ultrasound instrument with scan head adapted to be positioned adjacent said vessel, for generating a raster of pixels which defines a colour image representing flow velocities in said vessel through an image plane of said scan head;

b) sensor means connected to said scan head for measuring position and orientation of said scan head in three dimensions and generating a signal representative thereof;

c) computer means connected to said ultrasound instrument and said sensor means for receiving said raster of pixels and said signal representative of position and orientation of said scan head for determining position and orientation of the axis of said vessel in three-dimensions responsive to orientation of said image plane longitudinally of said vessel, determining an angle θ between said axis and said image plane responsive to orientation of said image plane transversally to said vessel, and calculating and displaying said volume flow measurement as a summation of said flow velocities scaled by the tangent of said angle θ.

2. The volume flow meter of claim 1, wherein said computer means calculates said volume flow by multiplying each of said flow velocities represented by respective ones of said pixels containing colour by respective values ΔA representing areas of said respective ones of said pixels in said image plane so as to generate respective pixel area-velocity products, summing said pixel area-velocity products for all of said pixels containing colour so as to generate a two-dimensional sum of pixel area-velocity products, and multiplying said two-dimensional sum of pixel area-velocity products by tanθ to generate said volume flow measurement.

3. The volume flow meter of claim 1, wherein said sensor means further comprises a transmitter positioned at a fixed location near said scan head for generating a pulsed DC magnetic field, and a receiver mounted on said scan head for detecting said magnetic field and sensing both location of the receiver in three-dimensions and orientation of the receiver relative to the transmitter, and in response generating said signal representative thereof.

4. The volume flow meter of claim 3, wherein said location is sensed in terms of X, Y and Z positional coordinates of the receiver with respect to the transmitter, and said orientation is sensed in terms of rotations about said Z, Y and X positional coordinates.

* * * * *